United States Patent [19]

Janssens et al.

[11] Patent Number: 4,897,401
[45] Date of Patent: Jan. 30, 1990

[54] N-(4-PIPERIDINYL) BICYCLIC CONDENSED 2-IMIDAZOLAMINE DERIVATIVES USEFUL IN TREATING ALLERGIC DISEASES

[75] Inventors: Frans E. Janssens, Bonheiden; Joseph L. G. Torremans, Beerse; Gaston S. M. Diels, Ravels, all of Belgium

[73] Assignee: Janssen Pharmaceutical N.V., Beerse, Belgium

[21] Appl. No.: 182,814

[22] Filed: Apr. 18, 1988

Related U.S. Application Data

[63] Continuation-in-part of Ser. No. 63,899, Jun. 19, 1987, abandoned.

[51] Int. Cl.$^4$ .................... A61K 31/44; C07D 471/04
[52] U.S. Cl. ................... 514/303; 514/234.2; 514/234.5; 514/316; 514/322; 544/127; 544/129; 546/118; 546/187; 546/199

[58] Field of Search ............... 544/127, 129; 546/118, 546/199, 187; 514/237, 253, 252, 303, 316, 322, 234.2, 234.5

[56] References Cited

U.S. PATENT DOCUMENTS

| | | | |
|---|---|---|---|
| 4,219,559 | 8/1980 | Janssens et al. | 546/118 |
| 4,556,660 | 12/1985 | Janssens et al. | 514/272 |
| 4,588,722 | 5/1986 | Janssens et al. | 546/118 |
| 4,634,704 | 1/1987 | Janssens et al. | 546/199 |
| 4,695,569 | 9/1987 | Janssens et al. | 514/258 |

*Primary Examiner*—Mary C. Lee
*Assistant Examiner*—Bernard Dentz
*Attorney, Agent, or Firm*—Charles J. Metz

[57] ABSTRACT

Novel N-(4-piperidinyl)bicyclic condensed 2-imidazolamine derivatives and their pharmaceutically acceptable acid addition salts having anti-histaminic properties, compositions containing the same, and methods of treating allergic diseases in warm-blooded animals.

10 Claims, No Drawings

N-(4-PIPERIDINYL) BICYCLIC CONDENSED 2-IMIDAZOLAMINE DERIVATIVES USEFUL IN TREATING ALLERGIC DISEASES

CROSS-REFERENCE TO RELATED APPLICATIONS

This is a continuation-in-part of our copending application Ser. No. 63,899 filed Jun. 19, 1987, now abandoned.

BACKGROUND OF THE INVENTION

In the U.S. Pat. No. 4,219,559 there are described a number of 1-substituted N-heterocyclyl-4-piperidinamines as compounds having useful anti-histaminic properties.

Further series of N-heterocyclyl-4-piperidinamines as compounds having useful anti-histaminic and serotonin-antagonistic properties have been described in U.S. Pat. Nos. 4,556,660, 4,634,704, 4,695,569 and 4,588,722.

The compounds of the present invention are substituted in a previously undisclosed manner and show favourable pharmacological properties.

DESCRIPTION OF THE INVENTION

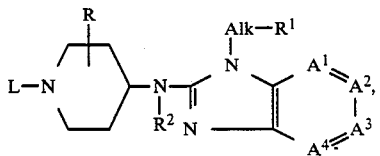  (I)

the pharmaceutically acceptable acid-addition salts and possible stereochemically isomeric forms thereof, wherein:

$A^1=A^2-A^3=A^4$ is a bivalent radical having the formula

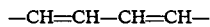  (a-1),

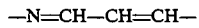  (a-2),

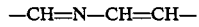  (a-3),

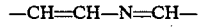  (a-4), or

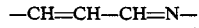  (a-5);

wherein one or two hydrogen atoms in said radicals (a-1)-(a-5) may, independently from each other, be replaced by halo, $C_{1-6}$alkyl, $C_{1-6}$alkyloxy, trifluoromethyl or hydroxy;

R is hydrogen or $C_{1-6}$alkyl;

$R^1$ is furanyl substituted with $C_{1-6}$alkyl, pyrazinyl, thiazolyl, or imidazolyl optionally substituted with $C_{1-6}$alkyl;

$R^2$ is hydrogen, $C_{1-6}$alkyl, $C_{3-6}$cycloalkyl, $Ar^3$-$C_{1-6}$alkyl or $(C_{1-6}alkyl)$-CO;

L is $C_{3-6}$alkenyl optionally substituted with $Ar^3$, or L is a radical of formula

  (b-1),

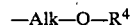  (b-2),

  (b-3),

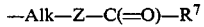  (b-4), or

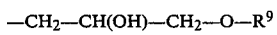  (b-5);

$R^3$ is hydrogen, $Ar^1$-thio, $Ar^3$-sulfonyl, 4,5-dihydro-5-oxo-1H-tetrazol-1-yl being optionally substituted in its 4-position with $Ar^3$ or $C_{1-6}$alkyl, 2,3-dihydro-1,4-benzodioxin-2-yl, 2,3-dihydro-1,4-benzodioxin-6-yl, 4-morpholinyl, 1-piperidinyl or 1-pyrrolidinyl, or when $R^1$ is furanyl substituted with $C_{1-6}$alkyl and $A^1=A^2-A^3=A^4$ is a bivalent radical of formula (a-1) or (a-2), $R^3$ may also be $Ar^1$, 2,3-dihydro-2-oxo-1H-benzimidazol-1-yl or 1-($C_{1-6}$alkyl)-pyrrolyl;

$R^4$ is $C_{1-6}$alkyl or $Ar^1$;

$R^5$ is $C_{1-6}$alkyl optionally substituted with $Ar^2$;

$R^6$ is $Ar^2$ or $C_{1-6}$alkyl optionally substituted with $Ar^2$ or when $A^1=A^2-A^3=A^4$ is a radical of formula (a-1) or (a-2), $R^6$ may also be 1H-benzimidazol-2-yl;

$R^7$ is $C_{1-6}$alkyl, $Ar^2$-$C_{1-6}$alkyl, $Ar^2$, amino, $Ar^2$-amino, mono- and di($C_{1-6}$alkyl)amino, mono- and di($Ar^2$-$C_{1-6}$alkyl)amino, 1-piperidinyl, 1-pyrrolidinyl, 4-morpholinyl, $C_{3-6}$cycloalkyloxy, $C_{1-6}$alkyloxy or $Ar^1$-$C_{1-6}$alkyloxy;

Z is O, $NR^8$ or a direct bond; said $R^8$ being hydrogen or $C_{1-6}$alkyl optionally substituted with $Ar^1$;

$R^9$ is $Ar^3$;

each Alk independently being $C_{1-6}$alkanediyl;

$Ar^1$ is phenyl, substituted phenyl, naphthalenyl, thienyl, halothienyl, $C_{1-6}$alkyl substituted thienyl or furanyl, wherein said substituted phenyl is phenyl substituted with 1, 2 or 3 substituents, each independently selected from the group consisting of halo, hydroxy, nitro, cyano, trifluoromethyl, $C_{1-6}$alkyl, $C_{1-6}$alkyloxy, $C_{1-6}$alkylthio, mercapto, $C_{1-6}$alkylsulfonyl, $C_{1-6}$alkylsulfonyl$C_{1-6}$alkyl, phenyl$C_{1-6}$alkylsulfonyl, phenylsulfonyl$C_{1-6}$alkyl, amino, mono- and di($C_{1-6}$alkyl)amino, carboxyl, $C_{1-6}$alkyloxycarbonyl and $C_{1-6}$alkylcarbonyl;

$Ar^2$ has the same meanings of $Ar^1$, and may also be pyridinyl, mono- and di($C_{1-6}$alkyloxy)pyridinyl or furanyl substituted with $C_{1-6}$alkyl; and $Ar^3$ has the same meanings of $Ar^2$, and may also be pyrazinyl, 1-($C_{1-6}$alkyl)pyrrolyl, thiazolyl or imidazolyl optionally substituted with $C_{1-6}$alkyl;

provided that $A^1=A^2-A^3=A^4$ is a radical of formula (a-1) or (a-2) when L is a radical of formula (b-4).

As used in the foregoing definitions the term halo is generic to fluoro, chloro, bromo and iodo; the term "$C_{1-6}$alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; the term "$C_{3-6}$cycloalkyl" is generic to cyclopropyl, cyclobutyl, cyclopentyl and cyclohexyl; the term "$C_{3-6}$alkenyl" is meant to include straight and branch chained hydrocarbon radicals containing one double bond and having from 3 to 6 carbon atoms such as, for example, 3-propenyl, 2-butenyl and the like, and when a $C_{3-6}$alkenyl is substituted on a heteroatom, then the carbon atom of said $C_{3-6}$alkenyl connected to said heteroatom preferably is saturated.

The compounds of formula (I) may also exist in hydrated or in solvent addition forms and said forms are intended to be included within the scope of the present invention.

An interesting subgroup among the compounds of formula (I) comprises those compounds of formula (I) wherein $A^1=A^2-A^3=A^4$ is a bivalent radical having the formula (a-1). Another interesting subgroup among the compounds of formula (I) comprises those compounds of formula (I) wherein $A^1=A^2-A^3=A^4$ is a bivalent radical having a formula (a-2) through (a-5), with (a-2) being the most interesting subgroup.

Preferred compounds within the invention are those compounds of formula (I) wherein R is hydrogen and $R^2$ is hydrogen or $C_{1-6}$alkyl.

Particularly preferred compounds within the invention are those preferred compounds of formula (I) wherein L is $C_{3-6}$alkenyl optionally substituted with phenyl or substituted phenyl, or wherein L is a radical of formula (b-1), (b-2), (b-4) or (b-5) wherein $R^3$ is as defined hereinabove, $R^4$ is $C_{1-6}$alkyl, phenyl or substituted phenyl, $R^7$ is phenyl, substituted phenyl or $C_{1-6}$alkyl optionally substituted with phenyl or substituted phenyl, $R^8$ is hydrogen or $C_{1-6}$alkyl, and $R^9$ is phenyl, substituted phenyl or naphthalenyl.

More particularly preferred compounds within the invention are those particularly preferred compounds of formula (I) wherein L is a radical of formula (b-1) or (b-2) wherein $R^3$ is hydrogen, phenylsulfonyl, 4,5-dihydro-5-oxo-1H-tetrazol-1-yl being optionally substituted in its 4-position with $C_{1-4}$alkyl, 2,3-dihydro-1,4-benzodioxin-2-yl, 4-morpholinyl, 1-piperidinyl or 1-pyrrolidinyl, or when $R^1$ is furanyl substituted with $C_{1-6}$alkyl and $A^1=A^2-A^3=A^4$ is a bivalent radical of formula (a-1) or (a-2), $R^3$ may also be 2,3-dihydro-2-oxo-1H-benzimidazol-1-yl, thienyl, furanyl, phenyl or substituted phenyl.

Especially preferred compounds within the invention are those more particularly preferred compounds of formula (I) wherein $A^1=A^2-A^3=A^4$ is a bivalent radical of formula (a-1) or (a-2) and L is a radical of formula (b-1) wherein $R^3$ is hydrogen or phenyl optionally substituted with halo, $C_{1-4}$alkyl, $C_{1-4}$alkyloxy or hydroxy.

A particular subgroup of compounds of formula (I) comprises those compounds, preferred, particularly preferred, more particularly preferred or especially preferred compounds wherein $R^1$ is furanyl substituted with $C_{1-6}$alkyl.

A more particular subgroup of compounds of formula (I) comprises those compounds, preferred, particularly preferred, more particularly preferred or especially preferred compounds of formula (I) wherein —Alk—$R^1$ is $C_{1-4}$alkyl-5-$C_{1-4}$alkyl-2-furanyl, $C_{1-4}$alkyl-4-$C_{1-4}$alkyl-2-furanyl, $C_{1-4}$alkyl-3-$C_{1-4}$alkyl-2-furanyl, $C_{1-4}$alkyl-2-$C_{1-4}$alkyl-3-furanyl, $C_{1-4}$alkyl-4-$C_{1-4}$alkyl-3-furanyl or $C_{1-4}$alkyl-5-$C_{1-4}$alkyl-3-furanyl.

The most preferred compounds within the invention are selected from the group consisting of 3-[(5-methyl-2-furanyl)methyl]-N-(1-methyl-4-piperidinyl)-3H-imidazo[4,5-b]pyridin-2-amine, the pharmaceutically acceptable acid addition salts and the stereochemically isomeric forms thereof.

In order to simplify the structural representations of the compounds of formula (I) and of certain precursors and intermediates thereof the

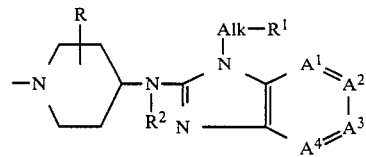

radical will hereafter be represented by the symbol D.

The compounds of formula (I) are generally prepared by N-alkylating a piperidine of formula (II) with a reagent of formula (III).

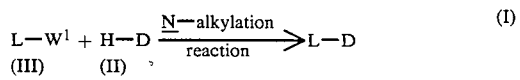

In formula (III) and in a number of the following intermediates W and $W^1$ represent an appropriate leaving group such as, for example, halo, preferably, chloro, bromo or iodo, or a sulfonyloxy group such as, for example, methylsulfonyloxy or 4-methylphenylsulfonyloxy, whereas W may also be $C_{1-6}$alkyloxy and $C_{1-6}$alkylthio.

The above N-alkylation reaction is conveniently conducted in an inert organic solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent e.g., N,N-dimethylformamide (DMF), N,N-dimethylacetamide (DMA), dimethyl sulfoxide (DMSO), nitrobenzene, 1-methyl-2-pyrrolidinone, and the like. The addition of an appropriate base such as, for example, an alkali or an earth alkaline metal carbonate, hydrogen carbonate, hydroxide, amide or hydride, e.g., sodium carbonate, sodium hydrogen carbonate, potassium carbonate, sodium hydroxide, calcium carbonate, calcium hydroxide, sodium hydride, sodium amide and the like, or an organic base, such as, for example, a tertiary amine, e.g., N,N-diethylethanamine, N-(1-methylethyl)-2-propanamine, 4-ethylmorpholine and the like may be utilized to pick up the acid which is liberated during the course of the reaction. In some instances the addition of a iodide salt, preferably an alkali metal iodide, is appropriate. Somewhat elevated temperatures may enhance the rate of the reaction.

The compounds of formula (I) wherein L is a radical of formula (b-1), (b-2), (b-3) or (b-4), said radical L being represented by the radical $L^1H$, and said compounds being represented by the formula (I-a), can also be prepared by the reductive N-alkylation reaction of (II) with an appropriate ketone or aldehyde of formula $L^1=O$ (IV), said $L^1=O$ being an intermediate of formula $L^1H_2$ wherein two geminal hydrogen atoms are replaced by $=O$, and $L^1=$ is a geminal bivalent radical comprising $R^3-C_{1-6}$alkylidene, $R^4-O-C_{1-6}$alkylidene, $R^6R^5-N-C_{1-6}$alkylidene and $R^7-C(=O)-Z-C_{1-6}$alkylidene.

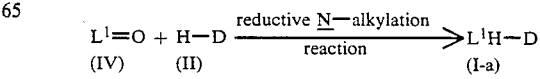

Said reductive N-alkylation reaction may conveniently be carried out by catalytically hydrogenating a mixture of the reactants in a suitable reaction-inert organic solvent according to art-known catalytic hydrogenating procedures. The reaction mixture may be stirred and/or heated in order to enhance the reaction rate. Suitable solvents are, for example, water; lower alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of two or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) wherein L is a radical of formula (b-2) wherein $R^4$ is $Ar^1$, said $R^4$ being represented by $R^{4-a}$ and said compounds by formula (I-b), may also be prepared by O-alkylating an intermediate of formula (V) with a reagent of formula (VI).

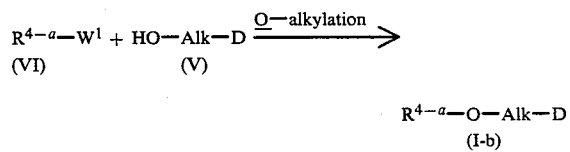

The compounds of formula (I-b) can also be prepared by O-alkylating an intermediate of formula (VII) with a reagent of formula (VIII).

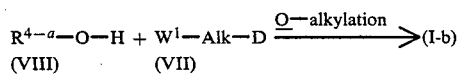

The O-alkylation ractions of (VI) with (V) and (VIII) with (VII) may be carried out by stirring the reactants, preferably at somewhat elevated temperatures in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a polar aprotic solvent, e.g., N,N-dimethylformamide; N,N-dimethylacetamide; dimethyl sulfoxide; nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction.

The compounds of formula (I) wherein L is a radical of formula (b-4) wherein Z is $NR^8$ or O, said Z being represented by $Z^1$ and $R^7$ is amino, $Ar^2$-amino, $C_{1-6}$alkyl-amino or $Ar^2$-$C_{1-6}$alkyl-amino, said $R^7$ being represented by $R^{7-a}$—NH—, and said compounds by formula (I-c-1), can be prepared by reacting an isocyanate of formula (X) with a reagent of formula (IX).

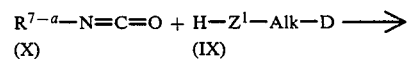

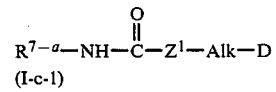

The compounds of formula (I), wherein L is a radical of formula (b-4) wherein Z is NH and $R^7$ is other than $Ar^2$ or $C_{1-6}$alkyl optionally substituted with $Ar^2$, said $R^7$ being represented by $R^{7-b}$, and said compounds being represented by formula (I-c-2), can be prepared by reacting an isocyanate of formula (XI) with a reagent of formula (XII).

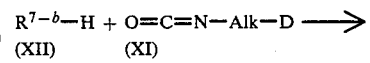

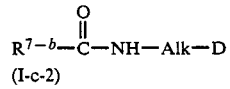

The reaction of (X) with (IX), or (XII) with (XI) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (b-4) wherein $R^7$ is $Ar^2$ or $C_{1-6}$alkyl optionally substituted with $Ar^2$, and Z is $NR^8$ or O, said $R^7$ being represented by $R^{7-c}$ and said compounds by formula (I-c-3), can be prepared by reacting a reagent of formula (XIII) or a functional derivative thereof with an intermediate of formula (IX).

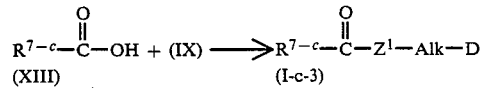

The reaction of (XIII) with (IX) may generally be conducted following art-known esterification- or amidation reaction procedures. For example, the carboxylic acid may be converted into a reactive derivative, e.g., an anhydride or a carboxylic acid halide, which subsequently, is reacted with (IX); or by reacting (XIII) and (IX) with a suitable reagent capable of forming amides or esters, e.g., dicyclohexylcarbodiimide, 2-chloro-1-methylpyridinium iodide and the like. Said reactions are most conveniently conducted in a suitable solvent such as, for example, an ether, e.g., tetrahydrofuran, a halogenated hydrocarbon, e.g., dichloromethane, trichloromethane or a polar aprotic solvent. The addition of a base such as, N,N-diethylethanamine may be appropriate.

The compounds of formula (I) wherein L is a radical of formula $L^2$-$C_{2-6}$alkanediyl, said $L^2$ being $Ar^1$-thio, $Ar^3$-sulfonyl, $Ar^2$, $C_{1-6}$alkylcarbonyl, $Ar^2$-$C_{1-6}$alkylcarbonyl, $Ar^2$-carbonyl, $C_{1-6}$alkyloxycarbonyl, $Ar^1$-$C_{1-6}$alkyloxycarbonyl or $C_{3-6}$cycloalkyloxycarbonyl, and said compounds being represented by formula (I-d), may be prepared by reacting an appropriate alkenylene of formula (XIV) with a piperidine of formula (II).

$L^2—C_{2-6}alkenediyl—H + H—D \longrightarrow L^2—C_{2-6}alkanediyl—D$
(XIV)            (II)            (I-d)

The compounds of formula (I) wherein L is a radical of formula (b-5), said compounds being represented by formula (I-e), may be prepared by reacting a reagent of formula (XV) with a piperidine of formula (II).

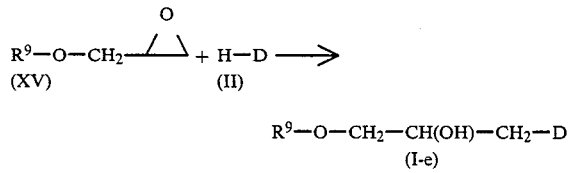

The reaction of (XIV) with (II), and (XV) with (II) may be conducted by stirring and, if desired, heating the reactants in a suitable solvent such as, for example, an alkanone, e.g., 2-propanone, 4-methyl-2-pentanone, an ether, e.g., tetrahydrofuran, 1,1'-oxybisethane, an alcohol, e.g., methanol, ethanol, 1-butanol, a polar aprotic solvent, e.g., N,N-dimethylformamide, N,N-dimethylacetamide and the like solvents.

Particular compounds wherein L is methyl, said compounds being represented by the formula (I-f), may also be prepared by reducing an intermediate of formula $C_{1-6}alkyl—O—C(=O)—D$ (XVI) with an appropriate reductant such as, for example, lithium tetrahydroaluminate in a suitable reaction-inert organic solvent, such as a lower alkanol.

The compounds of formula (I) can also be prepared by N-alkylating an intermediate of formula (XVII) with an appropriate reagent of formula (XVIII).

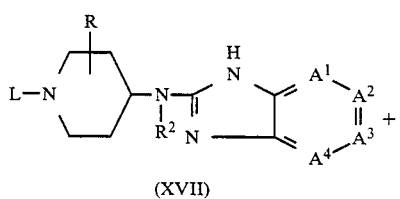

$W—Alk—R^1 \longrightarrow (I)$
(XVIII)

The said N-alkylation is conveniently carried out according to the procedures described hereinabove for the preparation of (I) starting from (III) and (II).

The compounds of formula (I) may alternatively be prepared by the cyclodesulfurization reaction of an appropriate thiourea derivative of formula (XIX), which may in situ be formed by condensing an isothiocyanate of formula (XX) with a diamine of formula (XXI)

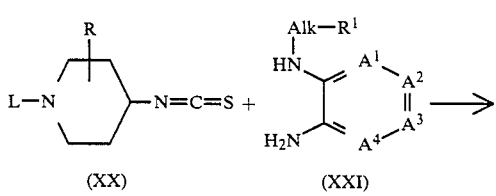

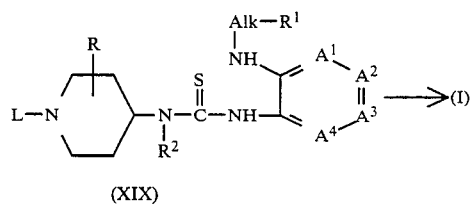

Said cyclodesulfurization reaction may be carried out by the reaction of (XIX) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (XIX) with an appropriate metal oxide or salt in an appropriate solvent according to art-known procedures. For example, the compounds of formula (I) can easily be prepared by the reaction of (XIX) with an appropriate Hg(II) or Pb(II) oxide or salt, such as, for example HgO, HgCl$_2$, Hg(OAc)$_2$, PbO or Pb(OAc)$_2$. In certain instances it may be appropriate to supplement the reaction mixture with a small amount of sulfur. Even so methanediimines, especially N,N'-methanetetraylbis[cyclohexanamine] may be used as cyclodesulfurizing agents.

Or, the compounds of formula (I) may be prepared by reacting a piperidine derivative of formula (XXII) with a benzimidazole derivative of formula (XXIII).

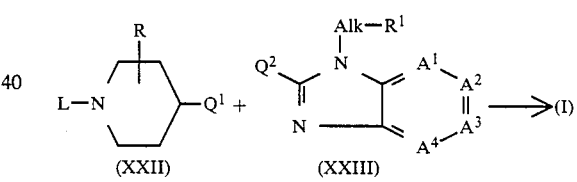

In (XXII) and (XXIII) $Q^1$ and $Q^2$ are selected so that during the reaction of (XXII) with (XXIII) the $—NR^2—$ moiety is formed connecting the piperidine and benzimidazole moiety. For example $Q^1$ may be a radical $—NHR^2$ and $Q^2$ a radical $—W$ or inversely $Q^1$ may be a radical $—W^1$ and $Q^2$ a radical $—NHR^2$.

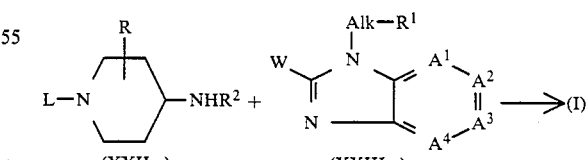

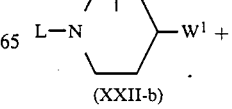

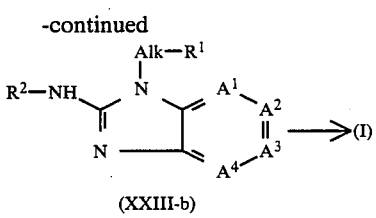

(XXIII-b)

The reactions of (XXII-a) with (XXIII-a) and of (XXII-b) with (XXIII-b) are conveniently conducted in an inert organic solvent such as, for example, an aromatic hydrocarbon, e.g., benzene, methylbenzene, dimethylbenzene; a lower alkanol, e.g., methanol, ethanol, 1-butanol; a ketone, e.g., 2-propanone, 4-methyl-2-pentanone; an ether, e.g., 1,4-dioxane, 1,1′-oxybisethane, tetrahydrofuran; N,N-dimethylformamide; N,N-dimethylacetamide; nitrobenzene; dimethyl sulfoxide; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of a iodide salt, preferably an alkali metal iodide, is appropriate. Somewhat elevated temperatures may enhance the rate of the reaction. Or, $Q^1$ may be an oxo radical and $Q^2$ a radical —NHR$^2$.

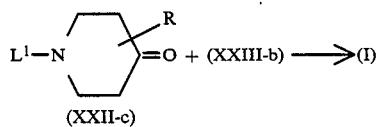

(XXII-c)

The reaction of (XXII-c) with (XXIII-b) is conveniently carried out by stirring the reactants, preferably at somewhat elevated temperatures, in a suitable reaction-inert organic solvent with an appropriate reductant. Preferably, the piperidone of formula (XXII-c) is first reacted with the benzimidazoleamine of formula (XXIII-b) to form an enamine, which optionally may be isolated and further purified, and subsequently subjecting the said enamine to a reduction reaction. Suitable solvents are, for example, water; lower alkanols, e.g., methanol, ethanol, 2-propanol; cyclic ethers, e.g., 1,4-dioxane; halogenated hydrocarbons, e.g., trichloromethane; N,N-dimethylformamide; N,N-dimethylacetamide; dimethyl sulfoxide and the like; or a mixture of such solvents. Appropriate reductants are for example, metal or complex metal hydrides, e.g. sodium borohydride, lithium aluminiumhydride; or hydrogen, the latter being preferably used in the presence of a suitable catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) can also be converted into each other following art-known procedures of functional group transformation. Some examples of such procedures will be cited hereinafter.

The hydrogen atom of the amino function(s) of compounds of formula (I) may be substituted following art-known procedures such as, for example, N-alkylation, N-acylation, reductive N-alkylation and the like procedures. For example alkylcarbonyl, arylcarbonyl and the like groups may be introduced by reacting the starting amine with an appropriate carboxylic acid or a derivative thereof such as, for example, an acid halide, acid anhydride and the like.

In all of the foregoing and in the following preparations, the reaction products may be isolated from the reaction mixture and, if desired, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some of the intermediates and starting materials in the foregoing preparations are known compounds while others are novel. They may be prepared according to art-known methodologies of preparing said known or similarly known compounds. Some procedures for preparing such intermediates will be described hereinafter in more detail.

The intermediates of formula (II) can conveniently be prepared following art-known procedures as described in, for example, U.S. Pat. Nos. 4,219,559, 4,556,660 and 4,588,722 which are incorporated herein by reference.

For example, by cyclodesulfurization of an intermediate of formula (XXIV) following the same procedures as described hereinabove for the preparation of (I) starting from (XIX) and, subsequently eliminating the protective group P in the thus obtained intermediate of formula (XXV).

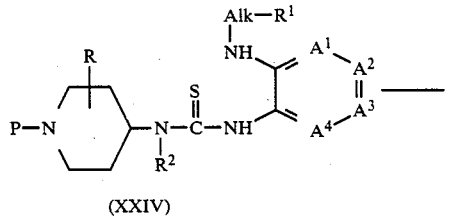

(XXIV)

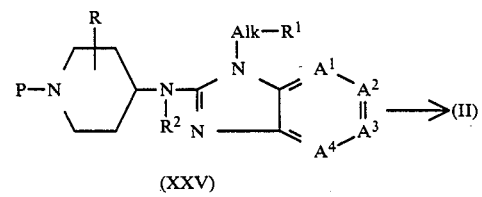

(XXV)

In (XXIV) and (XXV) P represents a protective group which is readily removeably by hydrogenation or hydrolysation, such as, phenylmethyl, $C_{1-4}$alkyloxycarbonyl, aryl$C_{1-4}$alkylalkyloxycarbonyl and the like groups.

The intermediates of formula (II) can also be prepared by reacting a piperidine derivative of formula (XXVI) with a benzimidazole derivative of formula (XXIII), following the same procedures as described hereinabove for the preparation of (I) starting from (XXII) and (XXIII) and, subsequently eliminating the protective group P in the thus obtained intermediate of formula (XXV).

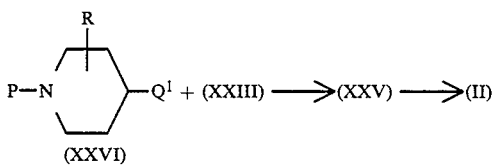

Intermediates of formulae (V), (VII), (IX) and (XI) can conveniently be prepared following art-known procedures as described in, for example, U.S. Pat. No. 4,556,660 by N-alkylating an intermediate of formula (II) with an appropriate reagent following a similar N-alkylation procedure as described hereinabove for the preparation of (I) starting from (II) and (III).

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Further, the compounds of this invention wherein L is $C_{3-6}$alkenyl optionally substituted with $Ar^3$ may be present as E- and Z-forms, this E- and Z-notation being in correspondence with the rules also described in J. Org. Chem., 35, 2849–2867 (1979).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), the pharmaceutically acceptable acid-addition salts and possible stereochemically isomeric forms thereof possess useful pharmacological properties. More particularly, they are active as anti-histaminics which activity is clearly evidenced by e.g. the results obtained in the "Protection of Rats from Compound 48/80-induced lethality"-test, the "Histamine antagonism in Guinea-Pig"-test and the "Ascaris Allergy test in Dogs"-test described in Arch. Int. Pharmacodyn. Ther. 251, 39-51 (1981). Apart from their anti-histaminic properties some of the subject compounds also show serotonin-antagonism.

Furthermore the compounds of formula (I), the pharmaceutically acceptable acid-addition salts and stereochemically isomeric forms thereof are particularly attractive due to their favourable pharmacokinetical profile. In particularly, some compounds show a rapid onset so that their anti-histaminic effects are almost instantaneously present.

In view of their anti-histaminic properties, the compounds of formula (I) and their acid-addition salts are very useful in the treatment of allergic diseases such as, for example, allergic rhinitis, allergic conjunctivities, chronic urticaria, allergic astma and the like.

In view of their useful pharmacological properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Those of skill in treating allergic diseases in warm-blooded animals could easily determine the effective amount from the test results presented hereinafter. In general it is contemplated that an effective amount would be from 0.001 mg/kg to 100 mg/kg body weight, and more preferably from 0.01 mg/kg to 1 mg/kg body weight.

The following examples are intented to illustrate and not to limit the scope of the present invention in all its aspects. Unless otherwise stated all parts therein are by weight.

EXPERIMENTAL PART

A. Preparation of Intermediates

EXAMPLE 1

(a) A mixture of 12.9 parts of 4-methyl-2-furancarboxaldehyde, 9.1 parts of hydroxylamine hydrochloride, 11.9 parts of pyridine and 160 parts of methanol was stirred overnight at room temperature. The reaction mixture was evaporated and the residue was taken up in water. The whole was acidified with concentrated hydrochloric acid and the product was extracted with 1,1'-oxybisethane. The extract was washed with water, dried, filtered and evaporated, yielding 14 parts (95.6%) of 4-methyl-2-furancarboxaldehyde,oxime as a residue (int. 1).

(b) A mixture of 14 parts of 4-methyl-2-furancarboxaldehyde,oxime, 400 parts of methanol and 40 parts of 2-propanol, saturated with hydrogen chloride was hydrogenated at normal pressure and at room temperature with 4 parts of palladium-on-charcoal catalyst 10%. After the calculated amount of hydrogen was taken up, the catalyst was filtered off and the filtrate was evaporated at 30° C. The residue was taken up in water and saturated with potassium carbonate. The product was extracted with 1,1'-oxybisethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated, yielding 8 parts (64.2%) of 4-methyl-2-furanmethanamine as a residue (int. 2).

(c) A mixture of 10.4 parts of 2-chloro-3-nitropyridine, 8 parts of 4-methyl-2-furanmethanamine, 7.6 parts of sodium hydrogen carbonate and 120 parts of ethanol was stirred overnight at reflux temperature. The reaction mixture was evaporated and the residue was taken up in water. The product was extracted with 1,1'-oxybisethane. The extract was dried, filtered and evaporated. The residue was purified by column chromatography over silica gel using trichloromethane as eluent. The pure fractions were collected and the eluent was evaporated, yielding 14.9 parts (91.2%) of N-[(4-methyl-2-furanyl)methyl]-3-nitro-2-pyridinamine as a residue (int. 3).

(d) A mixture of 14.9 parts of N-[(4-methyl-2-furanyl)methyl]-3-nitro-2-pyridinamine, 2 parts of a solution of thiophene in methanol 4% and 320 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated, yielding 14.2 parts (100%) of $N^2$-[(4-methyl-2-furanyl)methyl]-2,3-pyridinediamine as a residue (int. 4).

In a similar manner there were also prepared:
$N^1$-[(5-methyl-2-furanyl)methyl]-1,2-benzenediamine as a residue (int. 5);
$N^2$-[(5-methyl-2-furanyl)methyl]-2,3-pyridinediamine as a residue (int. 6);
$N^2$-[(2-methyl-3-furanyl)methyl]-2,3-pyridinediamine as a residue (int. 7);
$N^2$-[(5-ethyl-2-furanyl)methyl]-2,3-pyridinediamine as a residue (int. 8);
$N^4$-[(5-methyl-2-furanyl)methyl]-3,4-pyridinediamine as a residue (int. 9);
$N^2$-[(3-methyl-2-furanyl)methyl]-2,3-pyridinediamine as a residue (int. 10);
$N^3$-[(5-methyl-2-furanyl)methyl]-3,4-pyridinediamine as a residue (int. 11);
and $N^2$-[[5-(1-methylethyl)-2-furanyl]methyl]-2,3-pyridinediamine as a residue (int. 12).

EXAMPLE 2

(a) A mixture of 68.5 parts of ethyl 4-isothiocyanato-1-piperidinecarboxylate, 58.0 parts of $N^2$-[(5-ethyl-2-furanyl)methyl]-2,3-pyridinediamine and 450 parts of tetrahydrofuran was stirred overnight at reflux temperature. After evaporation, the residue was purified by column chromatography over silica gel using a mixture of trichloromethane and methanol (97:3 by volume) as eluent. The pure fractions were collected and the eluent was evaporated. The residue was stirred in 1,1'-oxybisethane. The product was filtered off and dried, yielding 50 parts (44.4%) of ethyl 4-[[[[2-[[(5-ethyl-2-furanyl)methyl]-amino]-3-pyridinyl]amino]thioxomethyl]amino]-1-piperidinecarboxylate (int. 13).

(b) A mixture of 50 parts of ethyl 4-[[[[2-[[(5-ethyl-2-furanyl)methyl]amino]-3-pyridinyl]amino]thioxomethyl]amino]-1-piperidinecarboxylate, 32.4 parts of mercury(II) oxide and 480 parts of ethanol was stirred for 1 hour at reflux temperature. The reaction mixture was filtered over diatomaceous earth and the filtrate was evaporated. The residue was stirred in 1,1'-oxybisethane. The crystallized product was filtered off and dried, yielding 38 parts (83.1%) of ethyl 4-[[3-[(5-ethyl-2-furanyl)methyl]-3H-imidazo[4,5-b]pyridin-2-yl]amino]-1-piperidinecarboxylate; mp. 111.1° C. (int. 14). In a similar manner there were also prepared:
ethyl 4-[[1-[(5-methyl-2-furanyl)methyl]-1H-benzimidazol-2-yl]amino]-1-piperidinecarboxylate hemihydrate; mp. 150.1° C. (int. 15);
ethyl 4-[[3-[(5-methyl-2-furanyl)methyl]-3H-imidazo[4,5-b]pyridin-2-yl]amino]-1-piperidinecarboxylate as a residue (int. 16);
ethyl 4-[[3-[(2-methyl-3-furanyl)methyl]-3H-imidazo[4,5-b]pyridin-2-yl]amino]-1-piperidinecarboxylate; mp. 153.7° C. (int. 17);
ethyl 4-[[1-[(5-methyl-2-furanyl)methyl]-1H-imidazo[4,5-c]pyridin-2-yl]amino]-1-piperidinecarboxylate; mp. 155.2° C. (int. 18);

ethyl 4-[[3-[(3-methyl-2-furanyl)methyl]-3H-imidazo[4,5-b]pyridin-2-yl]amino]-1-piperidinecarboxylate as a residue (int. 19);
ethyl 4-[[3-[(5-methyl-2-furanyl)methyl]-3H-imidazo[4,5-c]pyridin-2-yl]amino]-1-piperidinecarboxylate (int. 20);
ethyl 4-[[3-[[5-(1-methylethyl)-2-furanyl]methyl]-3H-imidazo[4,5-b]pyridin-2-yl]amino]1-piperidinecarboxylate as a residue (int. 21); and
ethyl 4-[[3-[(4-methyl-2-furanyl)methyl]-3H-imidazo[4,5-b]pyridin-2-yl]amino]-1-piperidinecarboxylate as a residue (int. 22).

EXAMPLE 3

To a stirred mixture of 4.6 parts of a sodium hydride dispersion 50% and 450 parts of N,N-dimethylformamide were added portionwise 57.6 parts of ethyl 4-(1H-benzimidazol-2-ylamino)-1-piperidinecarboxylate under nitrogen atmosphere. Upon complete addition, stirring was continued for 30 minutes at room temperature. 27.0 Parts of 3-(chloromethyl)-2-methylfuran were added dropwise while cooling. Upon completion, stirring was continued for 1 hour. Water was added dropwise to the mixture and the product was extracted with 4-methyl-2-pentanone. The extract was dried, filtered and evaporated. The residue was stirred in 1,1'-oxybisethane. The solid product was filtered off and purified by column chromatography over silica gel using a mixture of trichloromethane and methanol (95:5 by volume) as eluent. The pure fractions were collected and the eluent was evaporated. The residue was stirred in 1,1'-oxybisethane. The product was filtered off and dried, yielding 37.5 parts (19.0%) of ethyl 4-[[1-[(2-methyl-3-furanyl)methyl]-1H-benzimidazol-2-yl]amino]-1-piperidinecarboxylate; mp. 150.4° C. (int. 23).

In a similar manner there was also prepared: ethyl 4-[[1-(4-thiazolylmethyl)-1H-benzimidazol-2-yl]amino]-1-piperidinecarboxylate; mp. 156.2° C. (int. 24)

EXAMPLE 4

A mixture of 20.5 parts of ethyl 4-[[1-[(5-methyl-2-furanyl)methyl]-1H-imidazo[4,5-c]pyridin-2-yl]amino]-1-piperidinecarboxylate, 40 parts of potassium hydroxide and 240 parts of 2-propanol was stirred overnight at reflux temperature. After evaporation, the residue was taken up in water and the product was extracted with dichloromethane. The extract was dried, filtered and evaporated. The residue was crystallized from 2-propanone. The product was filtered off and dried, yielding 15 parts (88%) of 1-[(5-methyl-2-furanyl)methyl]-N-(4-piperidinyl)-1H-imidazo[4,5-c]pyridin-2-amine; mp. 185.6° C. (int. 25).

In a similar manner there were also prepared:
1-[(5-methyl-2-furanyl)methyl]-N-(4-piperidinyl)-1H-benzimidazol-2-amine as a residue (int. 26);
N-(4-piperidinyl)-1-(4-thiazolylmethyl)-1H-benzimidazol-2-amine dihydrobromide.monohydrate; mp. 223.5° C. (int. 27);
3-[(5-methyl-2-furanyl)methyl]-N-(4-piperidinyl)-3H-imidazo[4,5-b]pyridin-2-amine; mp. 120° C. (int. 28);
3-[(2-methyl-3-furanyl)methyl]-N-(4-piperidinyl)-3H-imidazo[4,5-b]pyridin-2-amine; mp. 165° C. (int. 29);
3-[(5-ethyl-2-furanyl)methyl]-N-(4-piperidinyl)-3H-imidazo[4,5-b]pyridin-2-amine; mp. 106° C. (int. 30);
1-[(2-methyl-3-furanyl)methyl]-N-(4-piperidinyl)-1H-benzimidazol-2-amine; mp. 168° C. (int. 31);
3-[(3-methyl-2-furanyl)methyl]-N-(4-piperidinyl)-3H-imidazo[4,5-b]pyridin-2-amine; mp. 160° C. (int. 32);
3-[(5-methyl-2-furanyl)methyl]-N-(4-piperidinyl)-3H-imidazo[4,5-c]pyridin-2-amine hemihydrate; mp. 146° C. (int. 33);
3-[[5-(1-methylethyl)-2-furanyl]methyl]-N-(4-piperidinyl)-3H-imidazo[4,5-b]-pyridin-2-amine dihydrochloride; mp. 235° C. (int. 34); and
3-[(4-methyl-2-furanyl)methyl]-N-(4-piperidinyl)-3H-imidazo[4,5-b]pyridin-2-amine; mp. 143° C. (int. 35).

EXAMPLE 5

(a) A mixture of 2 parts of 2-chloroacetonitrile, 8 parts of 1-[(5-methyl-2-furanyl)methyl]-N-(4-piperidinyl)-1H-benzimidazol-2-amine, 3.1 parts of sodium carbonate and 90 parts of N,N-dimethylformamide was stirred and heated overnight at 45° C. The reaction mixture was poured into water and the product was extracted with dichloromethane. The extract was dried, filtered and evaporated. The residue was crystallized from a mixture of acetonitrile and 2,2'-oxybispropane, yielding 7.3 parts (80.4%) of 4-[[1-[(5-methyl-2-furanyl)methyl]-1H-benzimidazol-2-yl]amino]-1-piperidineacetonitrile; mp. 177.3° C. (int. 36).

(b) A mixture of 6 parts of 4-[[1-[(5-methyl-2-furanyl)methyl]-1H-benzimidazol-2-yl]amino]-1-piperidineacetonitrile and 200 parts of methanol, saturated with ammonia was hydrogenated at normal pressure and at room temperature with 2 parts of Raney-nickel catalyst. After the calculated amount of hydrogen was taken up, the catalyst was filtered off and the filtrate was evaporated, yielding 6 parts of N-[1-(2-amino-ethyl)-4-piperidinyl]-1-[(5-methyl-2-furanyl)methyl]-1H-benzimidazol-2-amine as a residue (int. 37).

B. Preparation of Final Compounds

EXAMPLE 6

A mixture of 3.32 parts of 1-(2-bromoethyl)-4-ethyl-1,4-dihydro-5H-tetrazol-5-one, 4.65 parts of 1-[(5-methyl-2-furanyl)methyl]-N-(4-piperidinyl)-1H-benzimidazol-2-amine, 1.6 parts of sodium carbonate and 45 parts of N,N-dimethylacetamide was stirred overnight at 80° C. The reaction mixture was poured into water and the product was extracted with 4-methyl-2-pentanone. The extract was dried, filtered and evaporated. The residue was purified by filtration over silica gel using a mixture of trichloromethane and methanol (96:4 by volume) as eluent. The pure fractions were collected and the eluent was evaporated. The residue was converted into the ethanedioate salt in methanol. The salt was filtered off and dried, yielding 5.2 parts (55%) of 1-ethyl-1,4-dihydro-4-[2-[4-[[1-[(5-methyl-2-furanyl)methyl]-1H-benzimidazol-2-yl]amino]-1-piperidinyl]ethyl]-5H-tetrazol-5-one ethanedioate(1:2); mp. 190.5° C. (compound 22).

EXAMPLE 7

A mixture of 3.9 parts of 2,3-dihydro-1,4-benzodioxin-2-methanol methanesulfonate(ester), 7.4 parts of 3-[(5-methyl-2-furanyl)methyl]-N-(4-piperidinyl)-3H-imidazo[4,5-b]pyridin-2-amine, 5.3 parts of sodium carbonate and 90 parts of N,N-dimethylacetamide was stirred overnight at 80° C. The mixture was poured into water and the product was extracted with 4-methyl-2-pentanone. The extract was dried, filtered and evaporated. The residue was purified by column chromatography over silica gel using a mixture of trichloromethane and methanol (96:4 by volume) as eluent. The pure fractions were collected and the eluent was evaporated. The residue was converted into the ethanedioate salt in methanol. The salt was filtered off and dried, yielding 2.2 parts (23%) of N-[1-[(2,3-dihydro-1,4-benzodioxin-2-yl)methyl]-4-piperidinyl]-3-[(5-methyl-2-furanyl)methyl]-3H-imidazo[4,5-b]pyridin-2-amine ethanedioate(1:2); mp. 222.3° C. (compound 14).

EXAMPLE 8

A mixture of 1.2 parts of 1-chloro-2-ethoxyethane, 3.1 parts of 3-[(2-methyl-3-furanyl)methyl]-N-(4-piperidinyl)-3H-imidazo[4,5-b]pyridin-2-amine, 1.6 parts of sodium carbonate and 45 parts of N,N-dimethylformamide was stirred overnight at 70° C. The reaction mixture was poured into 50 parts of water. Petroleum ether was added and after stirring, the crystallized product was filtered off, washed with water and petroleum ether and stirred in 1,1'-oxybisethane. The product was filtered off and dried at room temperature, yielding 1.6 parts (38.1%) of N-[1-(2-ethoxyethyl)-4-piperidinyl]-3-[(2-methyl-3-furanyl)methyl]-3H-imidazo-[4,5-b]pyridin-2-amine dihydrate; mp. 84.5° C. (compound 32).

EXAMPLE 9

A mixture of 1.82 parts of 3-bromo-1-propene, 7.4 parts of 3-[(5-methyl-2-furanyl)methyl]-N-(4-piperidinyl)-3H-imidazo[4,5-b]pyridin-2-amine ethanedioate (2:1), 4.2 parts of sodium hydrogen carbonate and 120 parts of ethanol was stirred overnight at reflux temperature. The reaction mixture was filtered and the filtrate was evaporated. The residue was taken up in water and the product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the (E)-2-butenedioate salt in a mixture of 2-propanone and methanol. The salt was filtered off and dried, yielding 2 parts (23%) of 3-[(5-methyl-2-furanyl)methyl]-N-[1-(2-propenyl)-4-piperidinyl]-3H-imidazo-[4,5-b]pyridin-2-amine (E)-2-butenedioate(1:2); mp. 172.7° C. (compound 5).

EXAMPLE 10

A mixture of 2 parts of poly(oxymethylene), 4.5 parts of 3-[(5-methyl-2-furanyl)methyl]-N-(4-piperidinyl)-3H-imidazo[4,5-b]pyridin-2-amine, 1 part of a solution of thiophene in methanol 4% and 120 parts of methanol was hydrogenated at normal pressure and at 50° C. with 2 parts of platinum-on-charcoal catalyst 5%. After the calculated amount of hydrogen was taken up, the catalyst was filtered off over diatomaceous earth and the filtrate was evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 0.7 parts (14.3%) of 3-[(5-methyl-2-furanyl)methyl]-N-(1-methyl-4-piperidinyl)-3H-imidazo[4,5-b]pyridin-2-amine; mp. 131.0° C. (compound 1).

EXAMPLE 11

A mixture of 5 parts of a solution of acetaldehyde in tetrahydrofuran, 3.1 parts of 3-[(5-methyl-2-furanyl)methyl]-N-(4-piperidinyl)-3H-imidazo[4,5-b]pyridin-2-amine, 4.5 parts of tetrahydrofuran, 1 part of a solution of thiophene in methanol 4% and 200 parts of methanol was hydrogenated at normal pressure and at room temperature with 1 part of palladium-on-charcoal catalyst 10%. After the calculated amount of hydrogen was taken up, the catalyst was filtered off and the filtrate was evaporated. The residue was converted into the (E)-2-butenedioate salt in ethanol. The salt was filtered off and dried, yielding 2.2 parts (38.5%) of N-(1-ethyl-4-piperidinyl)-3-[(5-methyl-2-furanyl)methyl]-3H-imidazo[4,5-b]-pyridin-2-amine (E)-2-butenedioate(1:2); mp. 205.4° C. (compound 4).

EXAMPLE 12

A mixture of 1.1 parts of 3-butene-2-one, 4.7 parts of 3-[(5-methyl-2-furanyl)methyl]-N-(4-piperidinyl)-3H-imidazo[4,5-b]pyridin-2-amine and 120 parts of ethanol was stirred for 3 hours at reflux temperature. After evaporation, the residue was purified by column chromatography over silica gel using a mixture of trichloromethane and methanol (96:4 by volume) as eluent. The pure fractions were collected and the eluent was evaporated. The residue was converted into the ethanedioate salt in methanol. The salt was filtered off and dried overnight in vacuo at 100° C., yielding 1.8 parts (21.3%) of 4-[4-[[3-[(5-methyl-2-furanyl)methyl]-3H-imidazo[4,5-b]pyridin-2-yl]amino]-1-piperidinyl]-2-butanone ethanedioate(1:2); mp. 164.1° C. (compound 41).

EXAMPLE 13

A mixture of 4.5 parts of 2-(phenoxymethyl)oxirane, 4.65 parts of 1-[(5-methyl-2-furanyl)methyl]-N-(4-piperidinyl)-1H-benzimidazol-2-amine and 120 parts of methanol was stirred overnight at room temperature. The precipitated product was filtered off and dried, yielding 3.1 parts (44.8%) of 4-[[1-[(5-methyl-2-furanyl)methyl]-1H-benzimidazol-2-yl]amino]-α-(phenoxymethyl)-1-piperidineethanol; mp. 164.8° C. (compound 25).

EXAMPLE 14

A mixture of 0.7 parts of isocyanatomethane, 2.5 parts of N-[1-(2-aminoethyl)-4-piperidinyl]-1-[(5-methyl-2-furanyl)methyl]-1H-benzimidazol-2-amine and 135 parts of tetrahydrofuran was stirred for 3 hours at room temperature. The precipitated product was filtered off and dried, yielding 1.2 parts (41.1%) of N-methyl-N'-[2-[4-[[1-[(5-methyl-2-furanyl)methyl]-1H-benzimidazol-2-yl]amino]-1-piperidinyl]ethyl]urea; mp. 200.1° C. (compound 40).

EXAMPLE 15

To a stirred mixture of 11.5 parts of N-(1-methyl-4-piperidinyl)-1H-benzimidazol-2-amine and 144 parts of N,N-dimethylformamide were added 5 parts of a sodium hydride dispersion 50%. After stirring for 1 hour at room temperature, a solution of 12.8 parts of 2-(chloromethyl)pyrazine in N,N-dimethylformamide was added dropwise to the thus obtained mixture. Upon complete addition, stirring was continued for 2 hours at 50° C. The reaction mixture was poured into water and the product was extracted with trichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile. The product was filtered off and dried, yielding 1.5 parts (9.3%) of N-(1-methyl-4-piperidinyl)-1-(2-pyrazinylmethyl)-1H-benzimidazol-2-amine; mp. 169.3° C. (compound 69).

All other compounds listed in table 1 were obtained by analogous methods of preparation as described in examples 6–15, the actual method of preparation being indicated in column 2 ("Ex. no.").

TABLE 1

![Structure: piperidine with L-N, and Alk-R1, R2, N=A1-A2=A3-A4 ring]

| Comp. No. | Ex. No. | L | R² | Alk—R¹ | A¹=A²—A³=A⁴ | salt/base | mp (°C.) |
|---|---|---|---|---|---|---|---|
| 1 | 10 | CH₃— | H | CH₂—5-CH₃—2-furanyl | —N=CH—CH=CH— | base | 131.0 |
| 2 | 6 | 4-CH₃O—C₆H₄—CH₂—CH₂— | H | CH₂—5-CH₃—2-furanyl | —N=CH—CH=CH— | (E)-2-butenedioate(2:3) | 199.8 |
| 3 | 10 | (CH₃)₂—CH— | H | CH₂—5-CH₃—2-furanyl | —N=CH—CH=CH— | (E)-2-butenedioate(1:2) | 164.4 |
| 4 | 11 | CH₃—CH₂— | H | CH₂—5-CH₃—2-furanyl | —N=CH—CH=CH— | (E)-2-butenedioate(1:2) | 205.4 |
| 5 | 9 | CH₂=CH—CH₂— | H | CH₂—5-CH₃—2-furanyl | —N=CH—CH=CH— | (E)-2-butenedioate(1:2) | 172.7 |
| 6 | 6 | C₆H₅—CH=CH—CH₂— E form | H | CH₂—5-CH₃—2-furanyl | —N=CH—CH=CH— | 2(COOH)₂ | 203.6 |
| 7 | 6 | CH₃—CH₂—O—CH₂—CH₂— | H | CH₂—5-CH₃—2-furanyl | —N=CH—CH=CH— | 2(COOH)₂ | 204.0 |
| 8 | 6 | C₆H₅—O—(CH₂)₃— | H | CH₂—5-CH₃—2-furanyl | —N=CH—CH=CH— | ½ H₂O | 96.5 |
| 9 | 6 | ![benzimidazolone-CH₂-CH₂- group] | H | CH₂—5-CH₃—2-furanyl | —N=CH—CH=CH— | base | 238.5 |
| 10 | 6 | ![triazolone with CH₃—CH₂—N and N—CH₂—CH₂—] | H | CH₂—5-CH₃—2-furanyl | —N=CH—CH=CH— | 2(COOH)₂ | 194.1 |
| 11 | 11 | CH₃—CH₂— | H | CH₂—5-CH₃—2-furanyl | —CH=CH—CH=CH— | 2(COOH)₂ | 211.7 |
| 12 | 7 | ![2-thienyl-CH₂—CH₂—] | H | CH₂—5-CH₃—2-furanyl | —CH=CH—CH=CH— | 2(COOH)₂ | 224.8 |
| 13 | 6 | 4-CH₃O—C₆H₄—CH₂—CH₂— | H | CH₂—5-CH₃—2-furanyl | —CH=CH—CH=CH— | 2(COOH)₂ | 224.8 |
| 14 | 7 | ![1,4-benzodioxan-2-yl-CH₂—] | H | CH₂—5-CH₃—2-furanyl | —N=CH—CH=CH— | 2(COOH)₂ | 222.3 |

TABLE 1-continued

Structure:
L—N(piperidine)—N=C(R²)—N(Alk—R¹)—C=C fused to A¹=A²—A³=A⁴

| Comp. No. | Ex. No. | L | R² | Alk—R¹ | A¹=A²—A³=A⁴ | salt/base | mp (°C.) |
|---|---|---|---|---|---|---|---|
| 15 | 7 | thiophen-2-yl—CH₂—CH₂— | H | CH₂—5-CH₃—2-furanyl | —N=CH—CH=CH— | 2(COOH)₂ | 213.3 |
| 16 | 10 | CH₃— | H | CH₂—5-CH₃—2-furanyl | —CH=CH—CH=CH— | (E)-2-butenedioate(2:3) | 204.4 |
| 17 | 6 | CH₃—CH₂—O—CH₂—CH₂— | H | CH₂—5-CH₃—2-furanyl | —CH=CH—CH=CH— | (E)-2-butenedioate(2:3) | 175.9 |
| 18 | 6 | CH₃—C(=O)—(CH₂)₃— | H | CH₂—5-CH₃—2-furanyl | —N=CH—CH=CH— | 2(COOH)₂ | 190.1 |
| 19 | 6 | C₆H₅—O—(CH₂)₃— | H | CH₂—5-CH₃—2-furanyl | —CH=CH—CH=CH— | ½ H₂O | 125.0 |
| 20 | 6 | 2-(HN—C(=O))—C₆H₄—N—CH₂—CH₂— | H | CH₂—5-CH₃—2-furanyl | —CH=CH—CH=CH— | base | 211.7 |
| 21 | 6 | C₆H₅—CH=CH—CH₂— E form | H | CH₂—5-CH₃—2-furanyl | —CH=CH—CH=CH— | 2(COOH)₂ | 225.5 |
| 22 | 6 | CH₃—CH₂—N(C=O)—N=N—CH₂—CH₂— | H | CH₂—5-CH₃—2-furanyl | —CH=CH—CH=CH— | 2(COOH)₂ | 190.5 |
| 23 | 7 | 1,4-benzodioxin-2-yl—CH₂— | H | CH₂—5-CH₃—2-furanyl | —CH=CH—CH=CH— | 2(COOH)₂ | 216.2 |
| 24 | 6 | CH₃—C(=O)—(CH₂)₃— | H | CH₂—5-CH₃—2-furanyl | —CH=CH—CH=CH— | 2(COOH)₂ | 207.6 |
| 25 | 13 | C₆H₅—O—CH₂—CH(OH)—CH₂— | H | CH₂—5-CH₃—2-furanyl | —CH=CH—CH=CH— | base | 164.8 |
| 26 | 13 | C₆H₅—O—CH₂—CH(OH)—CH₂— | H | CH₂—5-CH₃—2-furanyl | —N=CH—CH=CH— | base | 147.2 |
| 27 | 6 | CH₃—CH₂—O—C(=O)—NH—(CH₂)₂— | H | CH₂—5-CH₃—2-furanyl | —CH=CH—CH=CH— | 2 H₂O | 124.3 |
| 28 | 9 | CH₂=CH—CH₂— | H | CH₂—5-CH₃—2-furanyl | —CH=CH—CH=CH— | base | 82.5 |
| 29 | 10 | CH₃— | H | CH₂—5-C₂H₅—2-furanyl | —N=CH—CH=CH— | base | 135.1 |
| 30 | 8 | CH₃—CH₂—O—CH₂—CH₂— | H | CH₂—5-C₂H₅—2-furanyl | —N=CH—CH=CH— | 2(COOH)₂ | 178.6 |
| 31 | 8 | 4-CH₃—O—C₆H₄—CH₂—CH₂— | H | CH₂—5-C₂H₅—2-furanyl | —N=CH—CH=CH— | base | 100.0 |

TABLE 1-continued

| Comp. No. | Ex. No. | L | R² | Alk—R¹ | A¹=A²—A³=A⁴ | salt/base | mp (°C.) |
|---|---|---|---|---|---|---|---|
| 32 | 8 | CH₃—CH₂—O—CH₂—CH₂— | H | CH₂—2-CH₃-3-furanyl | —N=CH—CH=CH— | 2 H₂O | 84.5 |
| 33 | 8 | 4-CH₃—O—C₆H₄—CH₂—CH₂— | H | CH₂—2-CH₃-3-furanyl | —N=CH—CH=CH— | base | 117.5 |
| 34 | 6 | CH₃—CH₂—O—C(=O)—NH—(CH₂)₂— | H | CH₂—5-CH₃-2-furanyl | —N=CH—CH=CH— | base | — |
| 35 | 14 | CH₃—NH—C(=O)—NH—(CH₂)₂— | H | CH₂—5-CH₃-2-furanyl | —N=CH—CH=CH— | base | 194.0 |
| 36 | 10 | CH₃— | H | CH₂—2-CH₃-3-furanyl | —N=CH—CH=CH— | 2 HCl.H₂O | 245.4 |
| 37 | 6 | CH₃—(CH₂)₃— | H | CH₂—5-CH₃-2-furanyl | —N=CH—CH=CH— | 2 (COOH)₂ | 202.0 |
| 38 | 6 | ![structure: HN-C(=O)-C₆H₄-N-CH₂-CH₂-CH₂—] | H | CH₂—5-CH₃-2-furanyl | —N=CH—CH=CH— | base | 201.0 |
| 39 | 6 | CH₃—(CH₂)₅— | H | CH₂—5-CH₃-2-furanyl | —N=CH—CH=CH— | 2(COOH)₂ | 192.2 |
| 40 | 14 | CH₃—NH—C(=O)—NH—(CH₂)₂— | H | CH₂—5-CH₃-3-furanyl | —CH=CH—CH=CH— | base | 200.1 |
| 41 | 12 | CH₃—(C=O)—NH—CH₂—CH₂— | H | CH₂—5-CH₃-2-furanyl | —N=CH—CH=CH— | 2(COOH)₂ | 164.1 |
| 42 | 6 | CH₃—(CH₂)₄— | H | CH₂—5-CH₃-2-furanyl | —N=CH—CH=CH— | (E)-2-butenedioate(2:3) | 188.5 |
| 43 | 10 | CH₃— | H | CH₂—5-CH₃-2-furanyl | —CH=CH—N=CH— | base | 179.9 |
| 44 | 6 | CH₃—CH₂—O—CH₂—CH₂— | H | CH₂—5-CH₃-2-furanyl | —CH=CH—N=CH— | base | 96.1 |
| 45 | 6 | CH₃—CH₂—O—CH₂—CH₂— | H | CH₂—2-CH₃-3-furanyl | —N=CH—CH=CH— | 2 H₂O | 110.7 |
| 46 | 6 | 4-F—C₆H₄—C(=O)—(CH₂)₃— | H | CH₂—5-CH₃-2-furanyl | —N=CH—CH=CH— | H₂O | 94.2 |
| 47 | 6 | CH₃—C(=O)—CH₂— | H | CH₂—5-CH₃-2-furanyl | —N=CH—CH=CH— | 2(COOH)₂ | 184.2 |
| 48 | 6 | 4-F—C₆H₄—C(=O)—(CH₂)₃— | H | CH₂—2-CH₃-3-furanyl | —CH=CH—CH=CH— | H₂O | 109.2 |
| 49 | 6 | 4-CH₃—O—C₆H₄—CH₂—CH₂— | H | CH₂—5-CH₃-2-furanyl | —CH=CH—N=CH— | base | 164.0 |
| 50 | 9 | CH₂=CH—(CH₂)₂— | H | CH₂—5-CH₃-2-furanyl | —CH=CH—CH=CH— | base | 165.8 |
| 51 | 10 | CH₃— | H | CH₂—5-CH₃-2-furanyl | —CH=CH—N=CH— | 2 H₂O | 102.3 |
| 52 | 6 | 4-CH₃—O—C₆H₄—CH₂— | H | CH₂—5-CH₃-2-furanyl | —N=CH—CH=CH— | (E)-2-butenedioate(2:3) | 218.8 |
| 53 | 6 | ![structure: HN-C(=O)-C₆H₄-N-CH₂-CH₂—] | H | CH₂—2-CH₃-3-furanyl | —N=CH—CH=CH— | base | 212.8 |

TABLE 1-continued

Structure:
L—N(piperidine)—with 4-position bearing N(Alk—R¹)—C(=NR²)—fused to ring A¹=A²—A³=A⁴

| Comp. No. | Ex. No. | L | R² | Alk—R¹ | A¹=A²—A³=A⁴ | salt/base | mp (°C.) |
|---|---|---|---|---|---|---|---|
| 54 | 6 | (benzimidazolinone)-N—CH₂—CH₂— | H | CH₂—5-C₂H₅—2-furanyl | —N=CH—CH=CH— | ½ H₂O | 94.4 |
| 55 | 10 | CH₃— | H | CH₂—5-CH₃—2-furanyl | —CH=N—CH=CH— | 2(COOH)₂ | 196.4 |
| 56 | 10 | CH₃— | H | CH₂—3-CH₃—2-furanyl | —N=CH—CH=CH— | base | 132.6 |
| 57 | 6 | CH₃—CH₂—O—CH₂—CH₂— | H | CH₂—5-CH₃—2-furanyl | —CH=N—CH=CH— | 2(COOH)₂ | 135.6 |
| 58 | 6 | 4-CH₃O—C₆H₄—CH₂—CH₂— | H | CH₂—5-iC₃H₇—2-furanyl | —N=CH—CH=CH— | 2HCl.H₂O | 198.0 |
| 59 | 6 | (benzimidazolinone)-N—CH₂—CH₂— | H | CH₂—5-iC₃H₇—2-furanyl | —N=CH—CH=CH— | base | 180.3 |
| 60 | 8 | CH₃—CH₂—O—CH₂—CH₂— | H | CH₂—5-iC₃H₇—2-furanyl | —N=CH—CH=CH— | (E)-2-butenedioate(1:2) | 181.0 |
| 61 | 10 | CH₃— | H | CH₂—5-iC₃H₇—2-furanyl | —N=CH—CH=CH— | 2 HCl | 257.1 |
| 62 | 10 | CH₃— | H | CH₂—4-CH₃—2-furanyl | —N=CH—CH=CH— | (E)-2-butenedioate(1:2) | 200.0 |
| 63 | 6 | (benzimidazolinone)-N—CH₂—CH₂— | H | CH₂—4-CH₃—2-furanyl | —N=CH—CH=CH— | base | 189.5 |
| 64 | 6 | 4-CH₃O—C₆H₄—CH₂—CH₂— | H | CH₂—4-CH₃—2-furanyl | —N=CH—CH=CH— | (E)-2-butenedioate(1:2) | 199.9 |

TABLE 1-continued

Structure: L-N(piperidine)-C(=N-Alk-R¹)(-N(R²)-)- with A¹=A²-A³=A⁴ ring

| Comp. No. | Ex. No. | L | R² | Alk—R¹ | A¹=A²—A³=A⁴ | salt/base | mp (°C.) |
|---|---|---|---|---|---|---|---|
| 65 | 9 | O(morpholine N—CH₂—CH₂—) | H | CH₂—5-CH₃—2-furanyl | —N=CH—CH=CH— | 3 HCl | 238.2 |
| 66 | 9 | C₆H₅—S—CH₂—CH₂— | H | CH₂—5-CH₃—2-furanyl | —N=CH—CH=CH— | 2(COOH)₂ | 200.8 |
| 67 | 11 | CH₃— | H | CH₂—4-thiazolyl | —CH=CH—CH=CH— | 2 HCl/H₂O | 186.6 |
| 68 | 9 | C₆H₅—SO₂—CH₂—CH₂— | H | CH₂—5-CH₃—2-furanyl | —N=CH—CH=CH— | 2(COOH)₂ | 221.9 |
| 69 | 15 | CH₃— | H | CH₂—2-pyrazinyl | —CH=CH—CH=CH— | base | 169.3 |
| 70 | 9 | (piperidine N—CH₂—CH₂—) | H | CH₂—5-CH₃—2-furanyl | —N=CH—CH=CH— | 3 HCl | 232.5 |

(C) Pharmacological Examples

The useful anti-histaminic properties of the compounds of formula (I) which can be used as the active ingredient in the formulations according to the present invention can be demonstrated by the following test procedure.

EXAMPLE 16

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240-260 g were used in the experiment. After overnight starvation the rats were transferred to conditioned laboratories (temp.=21±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The $ED_{50}$-values of the compounds of formula (I) are listed in table 2. Said $ED_{50}$-values are the values in mg/kg body weight at which the tested compounds protect 50% of the tested animals against compound 48/80-induced lethality.

TABLE 2

| No. | compound 48/80 lethality test in rats-$ED_{50}$ in mg/kg body weight |
| --- | --- |
| 1 | 0.005 |
| 4 | 0.0025 |
| 5 | 0.005 |
| 6 | 0.04 |
| 7 | 0.02 |
| 8 | 0.04 |
| 9 | 0.02 |
| 10 | 0.04 |
| 11 | 0.01 |
| 13 | 0.04 |
| 15 | 0.04 |
| 18 | 0.01 |
| 22 | 0.04 |
| 26 | 0.04 |
| 29 | 0.04 |
| 36 | 0.04 |
| 37 | 0.02 |
| 38 | 0.02 |
| 39 | 0.04 |
| 40 | 0.02 |
| 41 | 0.01 |
| 42 | 0.04 |
| 46 | 0.04 |
| 53 | 0.04 |
| 56 | 0.04 |
| 62 | 0.005 |
| 63 | 0.04 |
| 64 | 0.04 |

(D) Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or a pharmaceutically acceptable acid addition salt thereof.

EXAMPLE 17

ORAL DROPS 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. per ml. The resulting solution was filled into suitable containers.

EXAMPLE 18

ORAL SOLUTION 9 g of methyl 4-hydroxybenzoate and 1 g of propyl 4-hydroxy-benzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 20 mg of the active ingredient per teaspoonful (5 ml). The resulting solution was filled in suitable containers.

EXAMPLE 19

CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelating capsules, comprising each 20 mg of the active ingredient.

EXAMPLE 20

FILM-COATED TABLETS

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each containing 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propane-triol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 21

INJECTABLE SOLUTION 1.8 g methyl 4-hydroxybenzoate and 0.2 g propyl 4-hydroxybenzoate were dissolved in about 0.5 l of boiling water for injection. Aftercooling to about 50° C. there were added while stirring 4 g lactic acid, 0.05 g propylene glycol and 4 g of the A.I.. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

EXAMPLE 22

SUPPOSITORIES 3 g A.I. was dissolved in a solution of 3 g 2,3-dihydroxybutanedioic acid in 25 ml polyethylene glycol 400. 12 g Surfactant (SPAN ®) and triglycerides (Witepsol 555 ®) q.s. ad 300 g were molten together. The latter mixture was mixed well with the former solution. The thus obtained mixture was poured into moulds at a temperature of 37°~38° C. to form 100 suppositories each containing 30 mg of the active ingredient.

We claim:

1. A chemical compound of the formula:

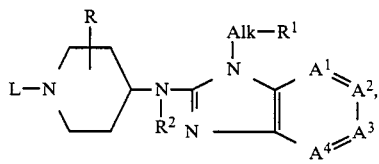

(I)

a pharmaceutically acceptable acid-addition salt or a stereochemically isomeric form thereof, wherein:

$A^1=A^2-A^3=A^4$ represents a bivalent group of the formula:

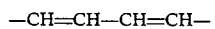 (a-1),

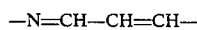 (a-2),

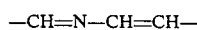 (a-3),

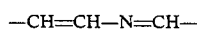 (a-4), or

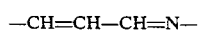 (a-5);

wherein one or two hydrogen atoms in said groups (a-1) through (a-5) may, independently from each other, be replaced by halo, $C_{1-6}$alkyl, $C_{1-6}$alkoxy, trifluoromethyl, or hydroxy;

Alk is $C_{1-6}$alkanediyl;

R is hydrogen;

$R^1$ is furanyl substituted with $C_{1-6}$alkyl;

$R^2$ is hydrogen or $C_{1-4}$alkyl; and

L is a group of the formula:

 (b-1);

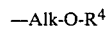 (b-2);

or

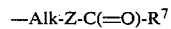 (b-4)

wherein Alk is $C_{1-6}$alkanediyl;

wherein $R^3$ is hydrogen, phenylsulfonyl, 4,5-dihydro-5-oxo-1H-tetrazol-1-yl being optionally substituted in its 4-position with $C_{1-4}$alkyl, 2,3-dihydro-1,4-benzodioxin-2-yl, 4-morpholinyl, 1-piperidinyl, or 1-pyrrolidinyl, or when $A^1=A^2-A^3=A^4$ is a bivalent group of formula (a-1) or (a-2), $R^3$ may also be 2,3-dihydro-2-oxo-1H-benzimidazol-1-yl, thienyl, furanyl, phenyl, or substituted phenyl;

wherein $R^4$ is $C_{1-6}$alkyl, phenyl, or substituted phenyl;

wherein $R^7$ is amino, mono- or di($C_{1-6}$alkyl)amino, $C_{1-6}$alkyloxy, phenyl, substituted phenyl, or $C_{1-6}$alkyl optionally substituted with phenyl or substituted phenyl; and wherein Z is O, $NR^8$, or a direct bond, wherein $R^8$ is hydrogen or $C_{1-6}$alkyl, provided that $A^1=A^2-A^3=A^4$ is a group of formula (a-1) or (a-2) when L is a group of formula (b-4), wherein said substituted phenyl is phenyl substituted with 1, 2, or 3 substitutents, each independently selected from the group consisting of halo, hydroxy, nitro, cyano, trifluoromethyl, $C_{1-6}$alkyl, $C_{1-6}$alkyloxy, $C_{1-6}$alkylthio, mercapto, $C_{1-6}$alkylsulfonyl, $C_{1-6}$alkylsulfonyl$C_{1-6}$alkyl, phenyl$C_{1-6}$alkylsulfonyl, phenylsulfonyl$C_{1-6}$alkyl, amino, mono- and di($C_{1-6}$alkyl)amino, carboxyl, $C_{1-6}$alkyloxycarbonyl, and $C_{1-6}$alkylcarbonyl.

2. A chemical compound according to claim 1 wherein —Alk—$R^1$ is $C_{1-4}$alkyl-5-$C_{1-4}$alkyl-2-furanyl, $C_{1-4}$alkyl-4-$C_{1-4}$alkyl-2-furanyl, $C_{1-4}$alkyl-3-$C_{1-4}$alkyl-2-furanyl, $C_{1-4}$alkyl-2-$C_{1-4}$alkyl-3-furanyl, $C_{1-4}$alkyl-4-$C_{1-4}$alkyl-3-furanyl or $C_{1-4}$alkyl-5-$C_{1-4}$alkyl-3-furanyl.

3. A chemical compound according to claim 2 wherein $A^1=A^2-A^3=A^4$ is a bivalent radical of formula (a-1) or (a-2) and L is a radical of formula (b-1) wherein $R^3$ is hydrogen or phenyl optionally substituted with halo, $C_{1-4}$alkyl, $C_{1-4}$alkyloxy or hydroxy.

4. A chemical compound according to claim 1 wherein the compound is 3-[(5-methyl-2-furanyl)methyl]-N-(1-methyl-4-piperidinyl)-3H-imidazo[4,5-b]pyridin-2-amine.

5. An anti-allergic composition comprising one or more pharmaceutical carriers and as active ingredient an anti-allergic effective amount of at least one compound of formula (I) as claimed in claim 1.

6. An anti-allergic composition according to claim 5 wherein $A^1=A^2-A^3=A^4$ is a bivalent radical of formula (a-1) or (a-2) and L is a radical of formula (b-1) wherein $R^3$ is hydrogen or phenyl optionally substituted with halo, $C_{1-4}$alkyl, $C_{1-4}$alkyloxy or hydroxy.

7. An anti-allergic composition according to claim 5 wherein the compound is 3-[(5-methyl-2-furanyl)methyl]-N-(1-methyl-4-piperidinyl)-3H-imidazo[4,5-b]pyridin-2-amine.

8. A method of treating allergic diseases in warm-blooded animals suffereing from the same, which method comprises the systemic administration to warm-blooded animals of an effective anti-allergic amount of a compound of formula (I) as claimed in claim 1.

9. A method according to claim 8 wherein $A^1=A^2-A^3=A^4$ is a bivalent radical of formula (a-1) or (a-2) and L is a radical of formula (b-1) wherein $R^3$ is hydrogen or phenyl optionally substituted with halo, $C_{1-4}$alkyl, $C_{1-4}$alkyloxy or hydroxy.

10. A method according to claim 8 wherein the compound is 3-[(5-methyl-2-furanyl)methyl]-N-(1-methyl-4-piperidinyl)-3H-imidazo[4,5-b]pyridin-2-amine.

* * * * *